(12) United States Patent
Gimvang

(10) Patent No.: US 7,884,089 B2
(45) Date of Patent: Feb. 8, 2011

(54) ANTIMICROBIAL COATING

(75) Inventor: Bo H. Gimvang, South Daytona, FL (US)

(73) Assignee: Xurex, Inc., Albuquerque, NM (US)

( * ) Notice: Subject to any disclaimer, the term of this patent is extended or adjusted under 35 U.S.C. 154(b) by 183 days.

(21) Appl. No.: 12/322,820

(22) Filed: Feb. 6, 2009

(65) Prior Publication Data

US 2009/0202656 A1  Aug. 13, 2009

Related U.S. Application Data

(60) Provisional application No. 61/027,345, filed on Feb. 8, 2008.

(51) Int. Cl.
| | |
|---|---|
| A01N 55/10 | (2006.01) |
| A01N 31/02 | (2006.01) |
| A01N 31/08 | (2006.01) |
| A01N 31/14 | (2006.01) |
| A01N 33/12 | (2006.01) |
| A01N 35/02 | (2006.01) |
| A01N 37/00 | (2006.01) |
| A01N 37/02 | (2006.01) |
| A01N 37/18 | (2006.01) |
| A01N 59/00 | (2006.01) |
| A01N 59/06 | (2006.01) |
| A01N 59/16 | (2006.01) |

(52) U.S. Cl. ............... 514/63; 514/241; 514/556; 514/557; 514/558; 514/617; 514/642; 514/643; 514/705; 514/717; 514/724; 514/726; 514/731; 514/736; 424/616; 424/618; 424/665; 424/688; 424/704; 106/287.11; 106/287.16

(58) Field of Classification Search ............... 514/63, 514/556, 642, 643; 424/616, 618, 665, 688, 424/704

See application file for complete search history.

(56) References Cited

U.S. PATENT DOCUMENTS

| | | | | |
|---|---|---|---|---|
| 5,954,869 | A * | 9/1999 | Elfersy et al. | 106/287.16 |
| 6,632,805 | B1 * | 10/2003 | Liebeskind et al. | 106/287.16 |
| 6,743,303 | B2 * | 6/2004 | Montano et al. | 148/256 |
| 6,994,890 | B2 * | 2/2006 | Ohlhausen et al. | 427/393.4 |
| 7,732,395 | B2 * | 6/2010 | Moses et al. | 510/384 |
| 2009/0108231 | A1 * | 4/2009 | Gimvang | 252/79.2 |
| 2010/0167613 | A1 * | 7/2010 | Higgins et al. | 442/123 |

OTHER PUBLICATIONS

Sauvet, G. et al., "Biocidal polymers active by contact. V. Synthesis of polysiloxanes with biocidal activity," Journal of Applied Polymer Science, vol. 75(8), pp. 1005-1012 (2000).*

El Ola, S.M.A. et al., "Unusual polymerization of 3-(trimethoxysilyl)-propyldimethyloctadecyl ammonium chloride on PET substrates," Polymer, vol. 45, pp. 3215-3225 (2004).*

* cited by examiner

Primary Examiner—John Pak

(57) ABSTRACT

An antimicrobial coating composition consisting essentially of 70 to 80 wt. percent water; 5 to 10 wt. percent methyl alcohol; 3 to 8 wt. percent octadecyl dimethyl trimethoxy silylpropyl-ammonium chloride; 1 to 5 wt. percent chloropropyl trimethoxysilane; 0.5 to 1.5 wt. percent aminopropyltrialkoxysilane; 0.5 to 1.5 wt. percent of a surfactant; 1 to 1.5 wt. percent of an anti-microbial agent; and 0.5 to 2.5 wt. percent sulfuric acid.

16 Claims, No Drawings

ANTIMICROBIAL COATING

This application claims the benefit of U.S. Provisional Patent Application Ser. No. 61/027,345, filed Feb. 8, 2008.

BACKGROUND

There is a need in the art for an antimicrobial coating for various surfaces, including, but not limited to concrete, wood, laminate, plastics, metals, ceramics, textiles, clothing and the like.

SUMMARY

An antimicrobial coating composition consisting essentially of 70 to 80 wt. percent water; 5 to 10 wt. percent methyl alcohol; 3 to 8 wt. percent octadecyl dimethyl trimethoxy silylpropyl-ammonium chloride; 1 to 5 wt. percent chloropropyl trimethoxysilane; 0.5 to 1.5 wt. percent aminopropyltrialkoxysilane; 0.5 to 1.5 wt. percent of a surfactant; 1 to 1.5 wt. percent of an anti-microbial agent; and 0.5 to 2.5 wt. percent sulfuric acid.

DETAILED DESCRIPTION

The present invention includes a series of formulations for an antimicrobial coating that can be applied to any number of potential surfaces. The coating(s) described herein are highly resistant to the growth of bacteria and viruses, and are thus well suited for use in hospitals, health clinics, restaurants, restrooms and other areas where the spread of microbial agents is a concern. In particular, the coating(s) described herein are adapted to prohibiting the growth and/or transmission of at least the following microbial agents: norovirus, methycilin, *staphylococcus aureus*, vancomycin, *enterococcus faecalis faecium*, hepatitis A and C, *mycobacterium tuberculosis*, human HIV-1 virus and the hepatitis B virus. The coating(s) described herein can also be used as a general purpose sterilizer.

A coating of a first preferred embodiment includes between seventy and eighty percent water by weight, such as distilled water or deionized water. The coating of the first preferred embodiment can also include methyl alcohol in an amount between five and ten percent by weight, as well as octadecyl dimethyl trimethoxy silylpropyl-ammonium chloride in an amount between three and eight percent by weight. The coating of the first preferred embodiment can also include chloropropyl trimethoxysilane in an amount between one and five percent by weight, and aminopropyltrialkoxysilane in an amount between one half percent and one and one half percent by weight. The coating of the first preferred embodiment can also include ethoxylated alkyl phenol or any other suitable surfactant in an amount between one half percent and one and one half percent by weight, as well as N,N-dimethyl ammonium-betaines in an amount between one and one and one half percent by weight. Other suitable microbial agents can include for example silver particles, other suitable betaines, or a combination of silver and one or more betaines. The coating of the first preferred embodiment can also include an acid, such as sulfuric acid, in an amount between one half percent and two and one half percent by weight. Other microbial additives and functional additives can be introduced in an amount between trace and two percent by weight, including for example hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and/or glutaraldehyde.

A method of making the coating of the first preferred embodiment can include the steps of providing an initial quantity of water that is anticipated to be between seventy and eighty percent of the total coating weight. Suitable water includes distilled water or deionized water. The method of making the coating of the first preferred embodiment can also include introducing into the mixture methyl alcohol in an amount between five and ten percent by weight of the final coating, as well as octadecyl dimethyl trimethoxy silylpropyl-ammonium chloride in an amount between three and eight percent by weight of the final coating. The method of making the coating of the first preferred embodiment can also include introducing chloropropyl trimethoxysilane in an amount between one and five percent by weight of the final coating, and aminopropyltrialkoxysilane in an amount between one half percent and one and one half percent by weight of the final coating. The method of making the coating of the first preferred embodiment can also include introducing N,N-dimethyl ammonium-betaines in an amount between one and one and one half percent by weight of the final coating. Other suitable microbial agents can include for example silver particles, other suitable betaines, or a combination of silver and one or more betaines. The method of making the coating of the first preferred embodiment can also include introducing an acid, such as sulfuric acid, in an amount between one half percent and two and one half percent by weight of the coating. The method of making the coating of the first preferred embodiment can also include the step of introducing ethoxylated alkyl phenol or any other suitable surfactant in an amount between one half percent and one and one half percent by weight of the final coating. Other microbial additives and functional additives can be introduced in an amount between trace and two percent by weight, including for example hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and/or glutaraldehyde. In one variation of the method described herein, the surfactant is the last material added into the coating composition.

As those of skill in the art will readily understand, the specific mixing times may be varied according to the mixing environment, temperature, humidity, air pressure, container characteristics and the desired functionality and/or features of the resulting coating, for example the desired hardness, chemical resistance, water repellant features and viscosity.

As a person skilled in the art will recognize from the previous detailed description and from the figures and claims, modifications and changes can be made to the preferred embodiments of the invention without departing from the scope of this invention defined in the following claims.

I claim:

1. An antimicrobial coating composition consisting of:
   70 to 80 wt. percent water;
   5 to 10 wt. percent methyl alcohol;
   3 to 8 wt. percent octadecyl dimethyl trimethoxy silylpropyl-ammonium chloride;
   1 to 5 wt. percent chloropropyl trimethoxysilane;
   0.5 to 1.5 wt. percent aminopropyltrialkoxysilane;
   0.5 to 1.5 wt. percent of a surfactant;

1 to 1.5 wt. percent of an anti-microbial agent; and
0.5 to 2.5 wt. percent sulfuric acid.

2. The coating composition of claim 1, wherein said surfactant is ethoxylated alkyl phenol.

3. The coating composition of claim 1, wherein said anti-microbial agent is N,N-dimethyl ammonium-betaines.

4. The coating composition of claim 1, wherein said anti-microbial agent is selected from the group consisting of silver particles, betaines, and combinations of silver particles and betaines.

5. The coating composition of claim 2, wherein said anti-microbial agent is N,N-dimethyl ammonium-betaines.

6. The coating composition of claim 2, wherein said anti-microbial agent is selected from the group consisting of silver particles, betaines, and combinations of silver particles and betaines.

7. An antimicrobial coating composition consisting essentially of:
   70 to 80 wt. percent water;
   5 to 10 wt. percent methyl alcohol;
   3 to 8 wt. percent octadecyl dimethyl trimethoxy silylpropyl-ammonium chloride;
   1 to 5 wt. percent chloropropyl trimethoxysilane;
   0.5 to 1.5 wt. percent aminopropyltrialkoxysilane;
   0.5 to 1.5 wt. percent of a surfactant;
   1 to 1.5 wt. percent of an anti-microbial agent; and
   0.5 to 2.5 wt. percent sulfuric acid.

8. The coating composition of claim 7, wherein said surfactant is ethoxylated alkyl phenol.

9. The coating composition of claim 7, wherein said anti-microbial agent is N,N-dimethyl ammonium-betaines.

10. The coating composition of claim 7, wherein said anti-microbial agent is selected from the group consisting of silver particles, betaines, and combinations of silver particles and betaines.

11. The coating composition of claim 7, further including up to 2 wt. percent of one or more additives selected from the group consisting of hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and glutaraldehyde.

12. The coating composition of claim 8, wherein said anti-microbial agent is N,N-dimethyl ammonium-betaines.

13. The coating composition of claim 8, wherein said anti-microbial agent is selected from the group consisting of silver particles, betaines, and combinations of silver particles and betaines.

14. The coating composition of claim 8, further including up to 2 wt. percent of one or more additives selected from the group consisting of hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and glutaraldehyde.

15. The coating composition of claim 9, further including up to 2 wt. percent of one or more additives selected from the group consisting of hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and glutaraldehyde.

16. The coating composition of claim 12, further including up to 2 wt. percent of one or more additives selected from the group consisting of hydrogen peroxide, peroxyacetic acid, sodium hypochlorite, sodium dichloroisocyanurate dihydrate, amyl phenol, phenylphenol, diisobutyl-phenoxy-ethoxyethyldimethylbenzyl ammonium chloride, para-tertiary amylphenol, citric acid, diethyl toluamide, octanoic acid, benzyl-4-chlorophenol, calcium hypochlorite, calcium oxide, sodium dichloro-s-triazinetrione, and glutaraldehyde.

\* \* \* \* \*